United States Patent [19]

Yokogawa et al.

[11] 4,364,926

[45] Dec. 21, 1982

[54] NOVEL ALKALINE PROTEASE M₃ METHOD FOR THE PREPARATION THEREOF AND DENTAL CARIES-PROPHYLACTIC COMPOSITION CONTAINING THE SAME

[75] Inventors: Kanae Yokogawa, Nara; Takeshi Yamamoto, Takatsuki; Yoshiyuki Takase, Amagasaki; Hiromi Katae, Kawachinagano; Shigeo Kawata, Kobe, all of Japan

[73] Assignee: Dainippon Pharmaceutical Co., Ltd., Osaka, Japan

[21] Appl. No.: 225,266

[22] Filed: Jan. 15, 1981

[30] Foreign Application Priority Data

Jan. 24, 1980 [JP] Japan .................. 55-007557

[51] Int. Cl.³ ................... C12N 9/50; C12N 9/52; A61K 7/28
[52] U.S. Cl. .................... 424/50; 435/219; 435/220; 435/886
[58] Field of Search ............... 435/219–225; 424/50

[56] References Cited

U.S. PATENT DOCUMENTS 3,713,983  1/1973  Yokotsuka et al. ........... 435/219 X
3,751,561  8/1973  Wildi et al. ................. 424/48
3,838,009  9/1974  Fukumoto et al. ............ 435/222
3,929,579  12/1975  Yoshimura et al. ........... 435/188

FOREIGN PATENT DOCUMENTS 1291922  9/1972  United Kingdom .

OTHER PUBLICATIONS

Abstract of Japanese Patent Application 21786/1971 (Derwent 41838S–BD).
Abstract of Japanese Patent Publication 21786/1971 (Derwent 41839S–BD).
Abstract of Japanese Patent Publication 4501/1972 (Derwent 35385R–B4D16).
Abstract of Japanese Patent Application 9870/1975 (Derwent 52357S–BCD).
Abstract of Japanese Patent Laid Open Application 92582/1973 (Derwent 20290 VII).

*Primary Examiner*—Lionel M. Shapiro
*Attorney, Agent, or Firm*—Wegner & Bretschneider

[57] ABSTRACT

Novel alkaline protease M₃ which is distinguished from known alkaline proteases in the phisiochemical properties, particularly in terms of the strong alkaline optimum pH: 9–12.5; being not inhibited by $FeSO_4$, diisopropyl fluorophosphate, ethylenediamine tetraacetate and iodoacetic acid; having glucosyltransferase inhibitory activity; and having the lowest molecular weight, and which can be produced by cultivating a microorganism of the genus Streptomyces, particularly *Streptomyces globisporus* B-1829 strain (ATCC 21553). The alkaline protease M₃ is useful for prevention of dental caries.

6 Claims, 6 Drawing Figures

NOVEL ALKALINE PROTEASE M₃ METHOD FOR THE PREPARATION THEREOF AND DENTAL CARIES-PROPHYLACTIC COMPOSITION CONTAINING THE SAME

The present invention relates to a novel alkaline protease $M_3$ which is useful for prevention of dental caries, a method for the preparation thereof, and a dental caries-prophylactic composition containing the alkaline protease $M_3$.

Various medicaments have hitherto been proposed and used for the prevention and treatment of the dental caries, but further development of improved medicaments has still been desired.

Generally, it is considered that the dental caries appears to arise in the following five stages:

(1) Cariogenic microorganisms such as *Streptococcus mutans* or *Streptococcus sanguis* grow in oral cavity by taking up sucrose derived from foods etc. as a nutrient source.

(2) The cariogenic microorganisms produce glucosyltranferase (hereinafter, referred to as "GTF") during growing.

(3) Sucrose contained in oral cavity is changed to water-soluble or insoluble polysaccharides such as dextrane by the action of GTF.

(4) The polysaccharides thus produced, particularly water-insoluble polysaccharides coat the surface of cariogenic microorganisms and other bacteria and finally adhere onto the tooth surface to form a dental plaque.

(5) Bacteria contained in the dental plaque produce acids such as lactic acid with utilization of saccharides, and the acids thus produced lyse tooth enamel, which results in appearance of dental caries.

Accordingly, the dental caries will be preventable by inhibiting the proceeding at any one of the above five stages. It is proposed in U.S. Pat. No. 3,751,561 and British Pat. No. 1,291,922 to destroy or remove food remnants or dental plaque by using proteases, particularly neutral protease, but these proteases show little effect for inhibiting dental caries.

As a result of intensive studies of the present inventors, it has been found that a certain alkaline protease is effective for inhibiting the activity of the above GTF which is one of the factors of forming dental caries.

An object of the present invention is to provide a novel alkaline protease useful for prevention of dental caries. Another object of the invention is to provide a method for the production of the novel alkaline protease. A further object of the invention is to provide a dental caries prophylactic composition containing said alkaline protease. These and other objects and advantages of the present invention will be apparent to persons skilled in the art from the following description.

The novel alkaline protease of the present invention shows excellent activities for inhibiting dental caries and has first been obtained by the present inventors by cultivating a certain microorganism and was designated as "alkaline protease $M_3$."

The chemical and physical properties of the alkaline protease $M_3$ are explained below with reference to the accompanying drawings.

The accompanying FIG. 1 shows a relation between the pH range and protease activity of the alkaline protease $M_3$.

Figure 1:
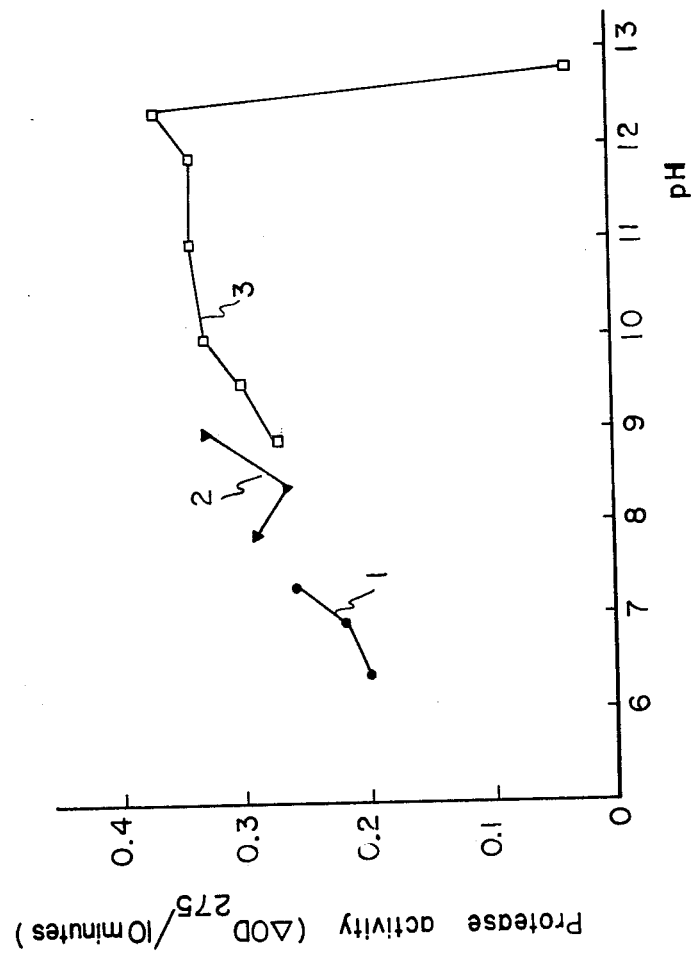
Figure 2:
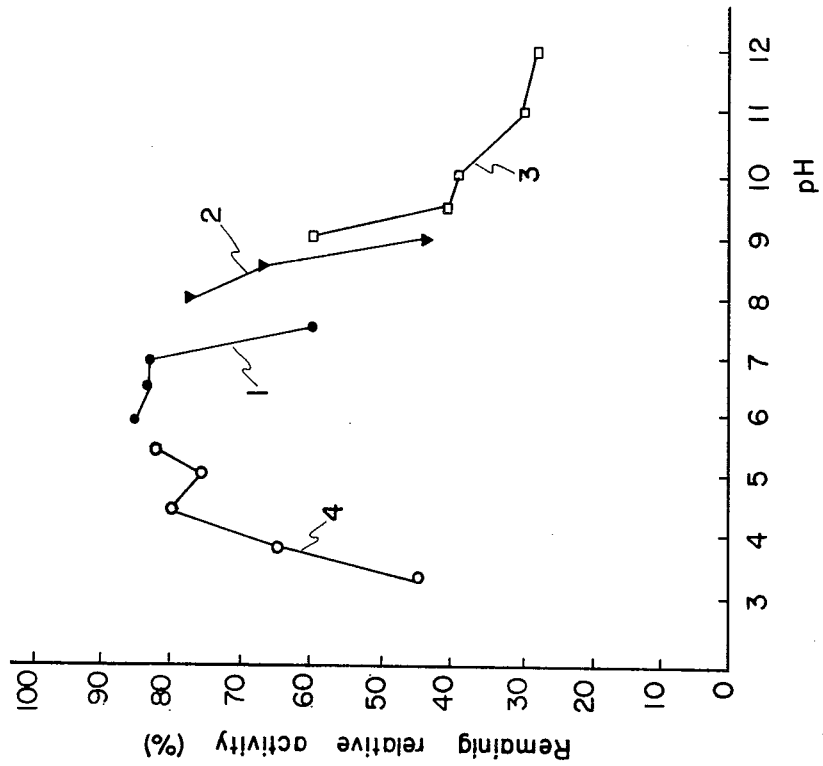
FIG. 2 shows a relation between the pH range and the remaining relative activity (i.e. the pH stability of the alkaline protease $M_3$).
Figure 6:
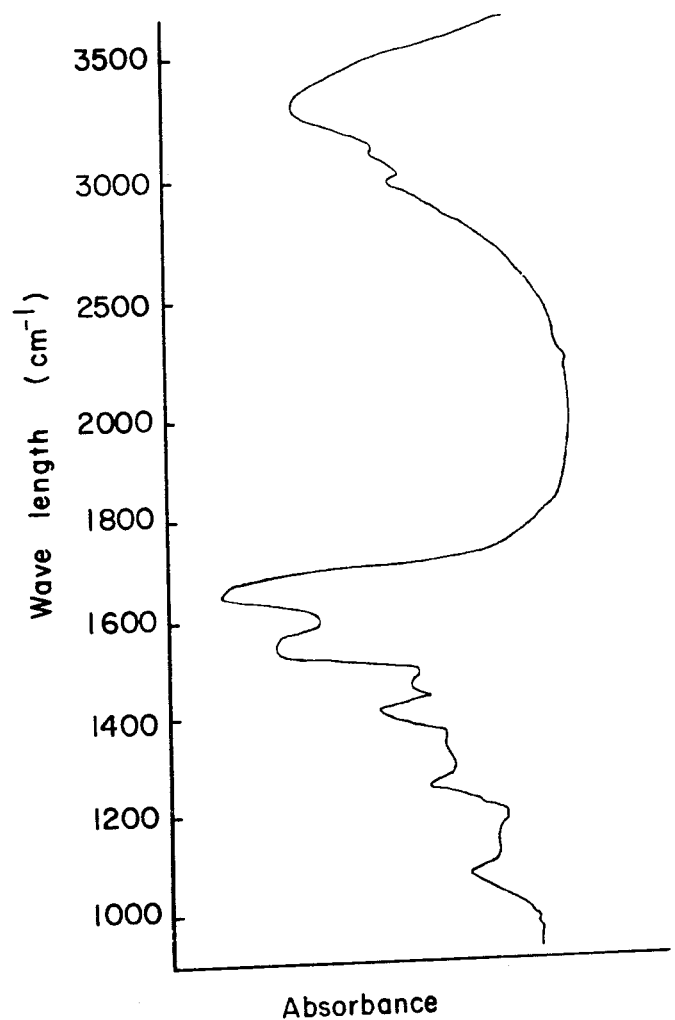

FIG. 6 shows the IR absorption spectrum of the alkaline protease $M_3$. In FIGS. 1 and 2, (1) is a phosphate buffer, (2) is a Tris-HCl buffer, (3) is a Sörensen buffer, and (4) is a citrate buffer. These buffer solutions were used in a concentration of 0.05 M in FIG. 1, and 0.02 M in FIG. 2.

(1) Activities

This enzyme is an alkaline protease which can hydrolyze casein and inhibits the activity of GTF. This enzyme has substantially no cariogenic microorganisms cell lytic activity, and in this respect, is different from the cell lytic enzyme disclosed in U.S. Pat. No. 3,929,579.

(2) Optimum pH and pH stability

As is shown in the accompanying FIG. 1, when casein is used as a substrate, this enzyme has an optimum pH at 9 to 12.5. Besides, as is shown in the accompanying FIG. 2, when this enzyme is kept in a buffer solution (pH 4–9) at 37° C. for 6 days, about 50% or more of the protease activity is retained.

(3) Optimum temperature and heat stability

Figure 3:
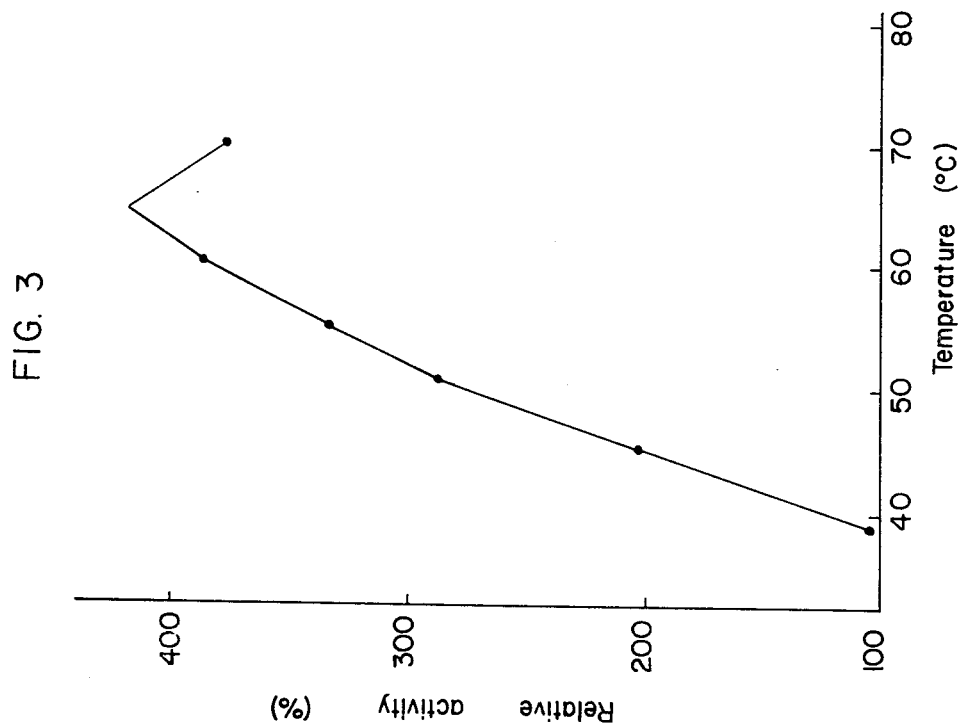
FIG. 3 shows a relation between the temperature and the relative activity (i.e. the temperature range, at which the alkaline protease $M_3$ shows its activity).

As is shown in the accompanying FIG. 3, when casein is used as a substrate, this enzyme shows an optimum temperature at about 65° C. Besides, as is shown in the accompanying FIG. 4, even when an aqueous solution of this enzyme is heated at 55° C. for 10 minutes, the protease activity is not lost.

(4) Conditions for inactivation

Figure 4:
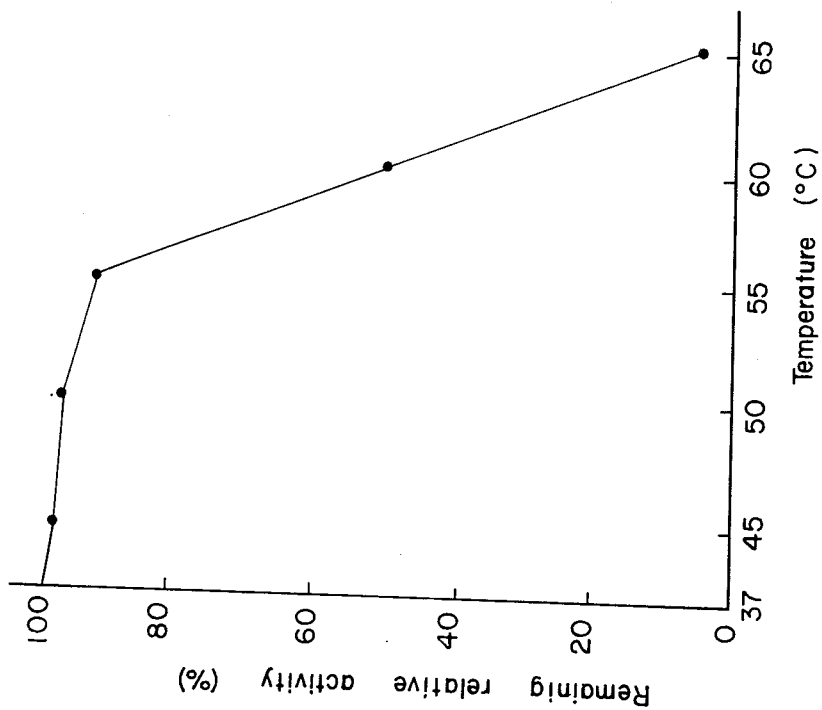
FIG. 4 shows a relation between the temperature and the remaining relative activity (i.e. the heat stability of the alkaline protease $M_3$).

As is shown in the accompanying FIG. 4, when an aqueous solution of this enzyme is heated at 60° C. for 10 minutes, about 50% or more of the protease activity is lost, and when the aqueous solution is heated at 65° C. for 10 minutes, more than 90% of the protease activity is lost.

(5) Effects of various additives

The protease activity of this enzyme is effected by various additives such as inhibitors and metal ions as shown in Table 1.

TABLE 1

| Additives[*1] | Relative activity (%) | Additives[*1] | Relative activity (%) |
|---|---|---|---|
| — | 100 | $CaCl_2$ | 78 |
| Succinic acid | 113 | $BaCl_2$ | 79 |
| Thiourea | 119 | $CoCl_2$ | 70 |
| Iodoacetic acid | 118 | $ZnSO_4$ | 69 |
| $Na_2HAsO_4$ | 111 | $NiCl_2$ | 62 |
| Semicarbazide hydrochloride | 116 | $FeSO_4$ | 95 |
| L-Ascorbic acid | 110 | $Fe_2(SO_4)_3$ | 95 |
| $NaN_3$ | 111 | $Pb(CH_3COO)_2$ | 64 |
| DFP[*2] | 86 | $Hg(CH_3COO)_2$ | 46 |
| NBS[*3] ($10^{-4}$M) | 0 | $CdCl_2$ | 42 |
| NBS[*3] ($10^{-3}$M) | 85 | $CuCl_2$ | 64 |

TABLE 1-continued

| Additives[*1] | Relative activity (%) | Additives[*1] | Relative activity (%) |
|---|---|---|---|
| $MnCl_2$ | 61 | EDTA[*4] | 87 |

[Remarks]:
[*1] Amount of the additives is $10^{-3}M$
[*2] DFP = Diisopropyl fluorophosphate
[*3] NBS = N—Bromosuccinimide
[*4] EDTA = Ethylenediamine tetraacetate As is clear from the above Table 1, the protease activity of this enzyme is substantially not inhibited by iodoacetic acid, DFP, $FeSO_4$ and EDTA in an amount of $10^{-3}M$, but is completely inhibited by NBS in an amount of $10^{-4}M$.

Moreover, when other additives than those shown in Table 1, such as 8-hydroxyquinoline, potassium oxalate, sodium diethyldithiocarbamate, sodium pyrophosphate, $Na_2HAsO_4$, $FCH_2COONa$, $NH_2OH.HCl$, thiosemicarbazide, $NH_2NH_2.HCl.\frac{1}{2}H_2SO_4$, $NaHSO_3$, $HSCH_2CH_2OH$, glutathione, L-cysteine hydrochloride, 2,3-dimercapto-1-propanol, NaF, trypsin-inhibitor, $MgCl_2$, $Li_2SO_4$ and $Ag_2SO_4$ are added in an amount of $10^{-3}M$, the relative protease activity of this enzyme is in the range of 85 to 110. That is, the protease activity of this enzyme is almost not effected by these additives.

(6) Isoelectric point

The isoelectric point of this enzyme is at about pH 9.5 [measured by using a carrier-ampholite (pH 2 to 11.5, made by LKB Produkter AB) at 300 V for 40 hours].

(7) Molecular weight

This enzyme has a molecular weight of about $1.7 \times 10^4$ [measured by a gel fitration method using Sephadex G-75 (made by Pharmacia Fine Chemicals)].

(8) UV absorption spectrum

Figure 5:
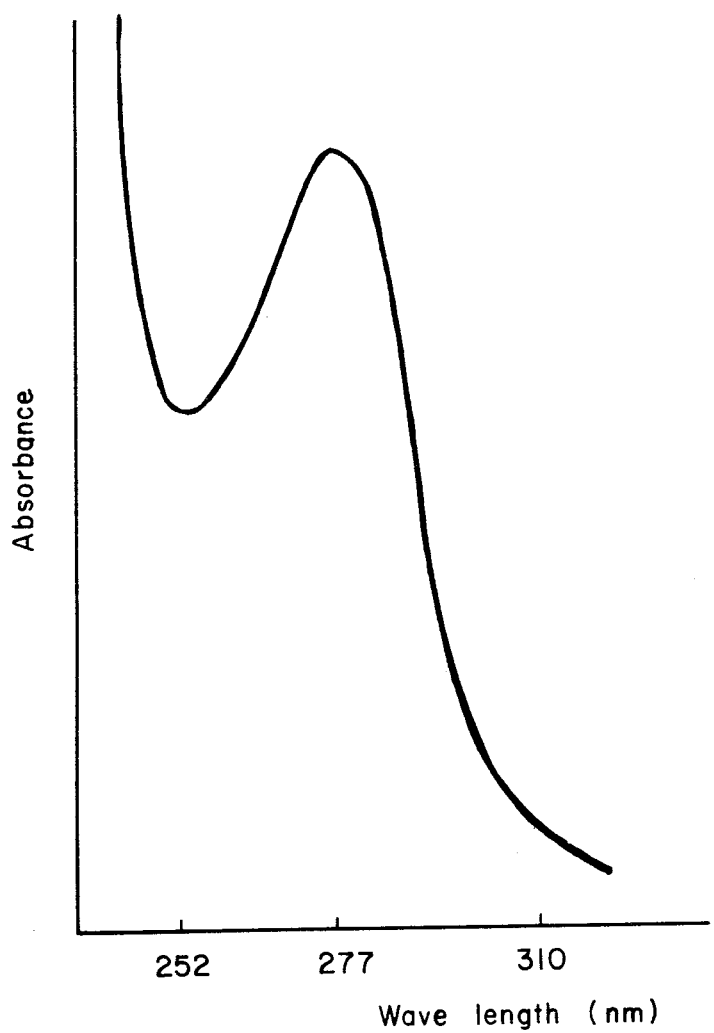
FIG. 5 shows the UV absorption spectrum of the alkaline protease $M_3$.

This enzyme shows the ultraviolet absorption spectrum as shown in the accompanying FIG. 5.

(9) IR absorption spectrum

This enzyme shows the infrared absorption spectrum as shown in the accompanying FIG. 6.

(10) Purification method

This enzyme can be purified in the manner as described in Example hereinafter.

(11) Measurement of activities (A) Protease activity

An appropriately diluted aqueous solution of alkaline protease $M_3$ (1 ml) is added to a 0.6% casein—0.05 M tris-HCl buffer solution (pH 8.0, 2 ml), and the mixture is kept at 37° C. for 10 minutes, and thereto is added a solution of reaction stopping agent (0.01 M trichloroacetic acid—0.02 M sodium acetate—0.03 M acetic acid) (3 ml). After removing the resulting precipitates by filtration, the absorbance of the filtrate is measured at 275 nm. From the resulting $UV_{275}$ value, the amount of tyrosine is calculated in the light of the $UV_{275}$ value of a standard tyrosine solution.

One unit of protease activity is defined as an amount of the enzyme which is necessary for increasing 1 μg of tyrosine in one minute.

(B) GTF inhibitory activity

Reagents (a) GTF solution:

$K_1$-R strain or AHT strain of *Streptococcus mutans* is cultivated on a trypticase-tryptose-yeast extract medium (pH 7.0) at 37° C. for 24 hours under stationary state. The culture broth is centrifuged, and to the supernatant is added 50% ammonium sulfate solution. The resulting precipitates are separated and are dissolved in a 0.05 M phosphate buffer (pH 6.8), followed by being subjected to dialysis against water. The resulting solution is used as a GTF solution.

(b) 5% sucrose—1/15 phophate buffer (pH 6.8);

(c) Alkaline protease $M_3$—1/15 M phosphate buffer (pH 6.8);

(d) 1/15 M phosphate buffer (pH 6.8);

(e) Anthrone solution:

Anthrone (recrystallized product, 200 mg) is dissolved in 95% sulfuric acid (100 ml) under cooling, and thereto is added water (20 ml) to give an anthrone solution.

Method

A mixtute of the reagents: (a) (0.1 ml), (b) (2.0 ml) and (c) (0.05 ml) is kept at 37° C. for 18 hours, and thereto is added ethanol so as to create a concentration of 70%, and the resulting mixture is allowed to stand at 4° C. for 2 hours. The resulting precipitates (polysaccharides) are separated by centrifugation and are dissolved in the reagent (d) (5.0 ml), followed by treating with ethanol in the same manner as described above. The resulting precipitates are again dissolved in the reagent (d) (5.0 ml). To the solution (0.1 ml) is added the reagent (e) (6.0 ml), and the mixture is shaken well and heated at 100° C. for 10 minutes. After cooling, the absorbance of the solution is measured at 620 nm, and the amount of polysaccharides is calculated.

The GTF activity is shown by the amount of the produced polysaccharides (μg/ml), and the GTF inhibitory activity is calculated by the following equation:

$$\text{Inhibitory rate (\%)} = \frac{A - B}{A} \times 100$$

wherein A is the GTF activity when no alkaline protease $M_3$ is added, and B is the GTF activity when alkaline protease $M_3$ is added.

These properties of the present alkaline protease $M_3$ are compared with those of the known alkaline proteases having an optimum pH of 10 more in the following Table 2.

TABLE 2

| Physicochemical properties | Alkaline protease $M_3$ | Alkaline proteases disclosed in literature:[*1] | | | | |
|---|---|---|---|---|---|---|
| | | 1 | 2 | 3 | 4 | 5 |
| Optimum pH | 9–12.5 | 10.5 | 11 | 10.7–11 | 10.5 | 11–12 |
| Optimum temperature (°C.) | 65 | 40–50 | 40–45 | 55 | 50–70 | About 60 |
| $\frac{\text{Activity at 65° C.}}{\text{Activity at optimum temp.}} \times 100 \, (\%)$ | 100 | 0 | 0 | —[*4] | — | 100 |

TABLE 2-continued

| Physicochemical properties | Alkaline protease $M_3$ | Alkaline proteases disclosed in literature:[*1] | | | | |
|---|---|---|---|---|---|---|
| | | 1 | 2 | 3 | 4 | 5 |
| $\frac{\text{Activity at pH 12.5}}{\text{Activity at optimum pH}} \times 100\ (\%)$ | 100 | Less than 30 | 0 | — | — | About 90 |
| Effect by $FeSO_4$ | Not inhibited | — | — | — | — | — |
| Effect by DFP[*2] | Not inhibited | — | — | Inhibited | Inhibited | Inhibited |
| Effect by EDTA[*3] | Not inhibited | Inhibited | Inhibited | Not inhibited | — | Not inhibited |
| Effect by iodoacetic acid | Not inhibited | — | — | — | — | — |
| Isoelectric point | About 9.5 | — | — | 9.75 | — | 10.6 |
| Molecular weight | About $1.7 \times 10^4$ | — | — | 25000 | 19500–20500 | 17500 |

[Remarks]:
[*1] References:
 1 = Japanese Patent Publication No. 21786/1971
 2 = Japanese Patent Publication No. 21787/1971
 3 = U.S. Pat. No. 3,838,009 and Japanese Patent Publication No. 4501/1972
 4 = U.S. Pat. No. 3,713,983 and Japanese Patent Publication No. 9870/1975
 5 = Japanese Patent Laid Open Application No. 92582/1973
[*2] DFP = Diisopropyl fluorophosphate
[*3] EDTA = Ethylenediamine tetraacetate
[*4] The symbol "—" means that no data is shown in the literatures.

Among the known alkaline proteases, the enzyme disclosed in the literature 5: Japanese Patent Laid Open Application No. 92582/1973 is most analogous to the alkaline protease $M_3$ of the present invention, but they are different from each other in the effect by DFP and isoelectric point.

Other than the above literature many references disclose various alkaline proteases, but they are also distinguishable from the present alkaline protease $M_3$. For instance, the alkaline proteases disclosed in Japanese Patent Publication Nos. 10193/1966, 10755/1969 and 5038/1971 show little protease activity at pH 12.5 and are different from the present alkaline protease $M_3$ in this point, and the alkaline proteases disclosed in Japanese Patent Publication Nos. 9230/1970 and 41594/1971 and Japanese Patent Laid Open Application No. 71191/1974 are inhibited in their activity by DFP and/or iodoacetic acid and are different from the present alkaline protease $M_3$ in this point.

Thus, the alkaline protease $M_3$ of the present invention is distinguished from the known alkaline proteases in the physicochemical properties as mentioned above and is a novel enzyme. Particularly, the present alkaline protease $M_3$ is distinguishable from the known alkaline protease in the following properties.

(i) It has an optimum pH at a strong alkaline range of 9 to 12.5.

(ii) The activity is substantially not inhibited by anyone of $FeSO_4$, DFP, EDTA and iodoacetic acid.

(iii) It has a GTF inhibitory activity.

(iv) It has the lowest molecular weight among the alkaline proteases.

The novel alkaline protease $M_3$ of the present invention can be produced by cultivating a microorganism of the genus Streptomyces being capable of producing alkaline protease $M_3$ and then harvesting the alkaline protease $M_3$ from the culture broth.

Suitable example of the microorganism of the genus Streptomyces is *Streptomyces globisporus* B-1829 strain which had been deposited to American Type Culture Collection, U.S. as ATCC 21553 and also to The Fermentation Research Institute, Agency of Industrial Science & Technology (BIKOKEN), Japanese as FERM-P 596. The physiological and morphological properties and cultivation conditions of this microorganism are disclosed in detail in U.S. Pat. No. 3,929,579.

The collection of the alkaline protease $M_3$ from the culture broth can be carried out by an appropriate combination of treatment with Amberlite CG-50 (made by Rohm and Haas Co.), salting out with ammonium sulfate, treatment with CM Sephadex C-25 (made by Pharmacia Fine Chemicals), treatment with carboxymethyl cellulose (CMC), or the like.

The above-mentioned *Streptomyces globisporus* B-1829 strain produces also cariogenic microorganisms cell lytic enzyme in addition to the alkaline protease $M_3$, but the enzymes can be separated from each other by applying the mixture to CM Sephadex C-25 or CMC column.

The alkaline protease $M_3$ of the present invention has excellent dental caries prophylactic activities and can be applied to human teeth for the purpose of the prevention of dental caries by conventional methods, conventional types of unit dosages or with conventional carriers or diluents. The conventional carriers or diluents are, for example, water, tooth powder, toothpaste, chewing gum, ointment, and the like. The enzyme of the present invention is incorporated into the compositions in an amount of 0.001 to 5% by weight, preferably 0.05 to 1% by weight.

In the preparation of toothpaste and tooth powder containing the present enzyme, conventional vehicles are used unless they give essentially undesirable effects to the activity of the enzyme. An appropriate water-insoluble polishing agent can be contained in the toothpaste and tooth powder. Suitable examples of the polishing agents are dicalcium phosphate, tricalcium phosphate, and the like. These polishing agents comprise usually a major proportion by weight of the solid ingredients. The content of the polishing agents is preferably about 30 to 60% by weight of the total composition in toothpaste and 85 to 95% by weight in tooth powder.

In the preparation of toothpaste, some plasticizers may also be added. Suitable examples of the plasticizers are water, glycerin, sorbitol, propylene glycol, monoglyceryl stearate, white petroleum jelly, cetyl alcohol, and the like, or a mixture thereof. The toothpaste is preferably incorporated with a gelling agent, such as sodium carboxymethyl cellulose, hydroxyethyl cellulose, polyvinyl pyrrolidone, gum tragacanth, and the like, and may also optionally be incorporated with other additional components, such as flavors, sweetening agents and coloring agents.

In the preparation of chewing gum containing the present enzyme, there may be used conventional gum base such as chicle resin, polyvinyl acetate, and the like. The chewing gum may also be incorporated with other conventional vehicles, such as plasticizers, softeners, sweetening agents, flavors and coloring agents.

Other means for using the present enzyme is a form of ointment. The teeth to be treated are applied with the ointment containing the present enzyme, followed by being rubbed up by finger or a toothbrush. The ointment can be prepared by conventional method using conventional vehicles which can be applied to the mouth unless they do not show inhibitory or destructive action onto the present enzyme. Suitable examples of materials to be used as an ointment base are sodium carboxymethyl cellulose, hydroxyethyl cellulose and Plastibase 50 W (dental paste base made by Squibb Co., Ltd.) which can form a jelly-like or creamy ointment.

The present enzyme can also be used in the form of a chewable tablet or troche. According to chewing or keeping the chewable tablet or troche containing the present enzyme in the mouth, the enzyme can sufficiently be in contact with teeth for a long period of time. The chewable tablet or troche can be prepared by conventional methods using conventional vehicles, suchas mannitol and sorbitol, and other conventional lubricating agents, sweetening agents, coloring agents, and the like.

The present enzyme may also be admixed with confectionary such as candy, cake, and the like. Moreover, the present enzyme may be administered in admixture with foodstuffs or beverage. In this case, the enzyme may be admixed with foodstuffs or beverage before or after processing thereof.

The preparation of alkaline protease $M_3$ of the present invention and compositions containing the same and also the activities of the present enzyme are illustrated by the following Examples and Experiments, but they should not be construed as limiting thereto.

EXAMPLE 1

Preparation of alkalne protease $M_3$

A culture broth was obtained by cultivating *Streptomyces globisporus* B-1829 strain (ATCC 21553) in a culture medium (pH 7.5) (70 liters) consisting of 2% dextrin, 0.5% soybean powder, 0.25% peptone, 0.5% $Na_2HPO_4$, 0.1% $KH_2PO_4$, 0.1% $MgSO_4$, and 0.5 NaCl in the same manner as disclosed in U.S. Pat. No. 3,929,579, and the culture broth thus obtained was filtered with a filter press to give a filtrate (70 liters).

To the filtrate was added Amberlite CG-50 ($H^+$type, made by Rohm and Haas Co., 2.8 kg), and the mixture was agitated for one hour to make the enzyme adsorb onto the resin. The resin was separated by centrifugation. To the resin adsorbing the enzyme was added 0.2 M $Na_2HPO_4$ (10 liters) and then the mixture was kept at pH 7.5 with aqueous ammonia and agitated for one hour, by which the enzyme was eluted. To the eluate (12 liters) was added solid ammonium sulfate so as to produce 60% saturation and the mixture was allowed to stand at 4° C. overnight. The resulting precipitates were separated by filtration and were dissolved in tap water (1.8 liter) to give an aqueous solution containing enzymes. The aqueous solution was adjusted to pH 2.0 with 1 N HCl and agitated at room temperaure for 30 minutes. After neutralizing to pH 6.0 with 1 N NaOH, the solution was dialyzed against running water to give a solution (2.3 liters).

The solution thus obtained was passed through a column (4×30 cm) packed with CM Sephadex C-25 ($Na^+$ type), and the column was washed with deionized water until absorption at 280 nm no more appeared. The column was then eluted with a linear gradient concentration, using 3 liters of water and 3 liters of 0.2 M phosphate buffer (pH 7.0). The fractions (about 400 ml) which were eluted at the concentration of buffer of about 0.03 to 0.05 M were collected. The collected fractions were desalted and concentrated with Dia-filter AS 201 (made by Bio Engineering Co., Ltd.). The concentrated solution (about 50 ml) was lyophilized to give alkaline protease $M_3$ (0.7 g). The enzyme had a protease activity of 730 U/mg.

According to amino acid analysis of this enzyme, it was composed of the amino acids components as shown in Table 3, wherein the data of the alkaline protease disclosed in Japanese Patent Laid Open Application No. 92582/1973 are also shown for comparison purpose.

TABLE 3

| Amino acid components | Alkaline protease $M_3$ | Alkaline protease disclosed in 92582/1973 |
|---|---|---|
| Aspartic acid | 15 | 19 |
| Threonine | 21 | 11 |
| Serine | 24 | 21 |
| Proline | 5 | 10 |
| Glutamic acid | 7 | 9 |
| Glycine | 27 | 24 |
| Alanine | 13 | 25 |
| Valine | 15 | 17 |
| Cystine | 2 | 0 |
| Methionine | 1 | 2 |
| Isoleucine | 4 | 6 |
| Leucine | 8 | 13 |
| Tyrosine | 8 | 5 |
| Phenylalanine | 6 | 1 |
| Tryptophan | 2 | 2 |
| Lysine | 2 | 3 |
| Histidine | 1 | 3 |
| Arginine | 8 | 5 |
| Molecular weight | 17,400 | 17,500 |

EXPERIMENT 1

GTF inhibitory activity

The inhibitory activity of alkaline protease $M_3$ and known proteases against GTF produced by $K_1$-R strain and AHT strain of *Streptococcus mutans* was measured in the manner as described hereinbefore. The proteases were used in an amount of 160 U/ml. The results are shown in Table 4.

TABLE 4

| Proteases (Optimum pH) | GTF by K₁-R strain | | Produced by AHT strain | |
|---|---|---|---|---|
| | Enzyme activity | Inhibitory rate (%) | Enzyme activity | Inhibitory rate (%) |
| — (control) | 577.5 | — | 580.0 | — |
| Alkaline protease M₃ (9–12.5) | 160.4 | 72.3 | 135.0 | 76.8 |
| Pronase (8.0) | 421.3 | 27.0 | 418.5 | 27.8 |
| α-Chymotrypsin (7.8) | 432.8 | 25.1 | 429.0 | 26.0 |
| Proctase (2.6) | 489.0 | 15.3 | 498.5 | 14.0 |
| Papaine (5.0) | 589.4 | −2.0 | 579.4 | 0 |
| Neutral protease* (7.0) | 520.0 | 10.0 | 532.4 | 8.2 |

*An enzyme produced by Bacillus subtilis

As is clear from the above Table 4, the alkaline protease $M_3$ of the present invention showed strong GTF inhibitory activity. As is mentioned hereinbefore, the measurement of the GTF inhibitory activity was carried out at pH 6.8, at which a neutral protease will show a high activity, nevertheless the neutral protease did almost not show GTF inhibitory activity. Besides, the known alkaline proteases, pronase and α-chymotrypsin, showed merely weak GTF inhibitory activity.

EXPERIMENT 2

Inhibition of dental caries

A group (10 animals) of golden hamsters (three weeks age) were fed on cariogenic diet No. 2000 (cf. Archives of Oral Biology, 9, 377–400, 1964) for one week. A culture of Streptococcus murant AHT strain was inoculated to the hamsters within both cheek pouches in an amount of 0.1 ml.

The hamsters were further fed on the above cariogenic diet No. 2000 containing proteases for 4 weeks. Thereafter, the dental caries of molar tooth of the hamsters was scored by the method of P. H. Keyes et al. (cf. J. Dental Research, 23, 439–444, 1944). The sample number of the molar tooth was blinded to the persons who observed the results. The results are shown in Table 5.

TABLE 5

| Proteases | | Inhibition of dental caries | |
|---|---|---|---|
| Kind (Optimum pH) | Amount (U/g) | Score | Inhibitory rate*² (%) |
| Alkaline protease M₃ (9–12.5) | 600 | 62.81 ± 7.12*³ | 42.5 |
| | 1200 | 41.29 ± 4.03*³ | 62.2 |
| | 2400 | 10.16 ± 3.24*³ | 90.7 |
| Pronase (8.0) | 600 | 109.15 ± 8.43*⁴ | 0.1 |
| | 1200 | 93.55 ± 6.98*⁴ | 14.4 |
| α-Cymotrypsin (7.8) | 600 | 109.82 ± 8.12*⁴ | −0.5 |
| | 1200 | 99.60 ± 6.74*⁴ | 8.8 |
| Proctase (2.6) | 600 | 108.93 ± 6.23*⁴ | 0.3 |
| | 1200 | 110.54 ± 5.38*⁴ | −1.2 |
| Papaine (5.0) | 600 | 110.13 ± 7.82*⁴ | −0.8 |
| | 1200 | 115.20 ± 8.68*⁴ | −5.5 |
| Neutral protease*¹ (7.0) | 600 | 110.23 ± 7.84*⁴ | −0.9 |
| | 1200 | 110.00 ± 8.23*⁴ | −0.7 |
| — (control) | — | 109.24 ± 4.19*⁴ | (0) |

[Remarks]:
*¹An enzyme produced by Bacillus subtilis
*²The inhibitory rate was calculated by the following equation:

$$\text{Inhibitory rate} = \frac{A - B}{A} \times 100$$

A: Score of the control
B: Score when the protease was added.
*³Significant difference from control, $P < 0.01$
*⁴Not significant from control As is clear from the above data, the alkaline protease $M_3$ of the present invention showed extremely excellent dental caries inhibitory activity, but on the other hand, the known protease did not show dental caries inhibitory activity.

EXAMPLE 2

A toothpaste having the following prescription was prepared in the usual manner.

| | % by weight |
|---|---|
| Glycerin | 25.70 |
| Sodium carboxymethyl cellulose | 0.95 |
| Distilled water | 20.15 |
| Dicalcium phosphate | 46.00 |
| Calcium carbonate | 5.80 |
| Saccarin | 0.25 |
| Flavor | 0.65 |
| Alkaline protease M₃ obtained by Example 1 | 0.005 |
| total | 100.00 |

EXAMPLE 3

A tooth powder having the following prescription was prepared in the usual manner.

| | % by weight |
|---|---|
| Sodium lauryl sulfate | 0.3 |
| Sodium carboxymethyl cellulose | 1 |
| Disodium hydrogen phosphate | 2 |
| Saccharin | 0.2 |
| Flavor | 1.8 |
| Alkaline protease M₃ obtained by Example 1 | 0.5 |
| Dicalcium phosphate | balance |

What is claimed is:
1. Alkaline protease $M_3$ which has the following chemical and physical properties:
   (1) Activities: It can hydrolyze casein and inhibits the activity of glucosyltransferase.
   (2) Optimum pH and pH stability: It has an optimum pH range of 9 to 12.5 (substrate: casein), and when it it kept in a buffer solution (pH 4–9) at 37° C. for 6 days, about 50% or more of the protease activity is remained.
   (3) Optimum temperature and heat stability:
   It has an optimum temperature of about 65° C. (substrate: casein), and even when an aqueous solution of this enzyme is heated at 55° C. for 10 minutes, it is stable.
   (4) Conditions for inactivation: When an aqueous solution of this enzyme is heated at 60° C. for 10 minutes, about 50% of the protease activity is lost, and when the aqueous solution is heated at 65° for 10 minutes, 90% or more of the activity is lost (5) Effects of various additives: The protease activity of this enzyme is completely inhibited by $10^{-4}$M of N-bromosuccinimde, but is almost not inhibited by $10^{-3}$M of iodoacetic acid, diisopropyl fluorophosphate, ethylenediamine tetraacetate, and $FeSO_4$.

(6) Isoelectric point: about pH 9.5

(7) Molecular weight: about $1.7 \times 10^4$.

2. A method for the preparation of alkaline protease $M_3$, which comprises cultivating a microcroorganism of the genus Streptomyces being capable of producing alkaline protease $M_3$ of claim 1 and isolating the alkaline protease $M_3$ from the culture broth.

3. A method according to claim 2, wherein the microorganism is a species of *Streptomyces globisporus*.

4. A method according to claim 2, wherein the microorganism is a strain of *Streptomyces globisporus* B-1829 (ATCC 21553).

5. A composition for prevention of dental caries comprising alkaline protease $M_3$ of claim 1 in admixture with conventional carrier of diluent.

6. A composition accorging to claim 5, wherein the alkaline protease $M_3$ is contained in an amount of from 0.001 to 5% by weight.

* * * * *